United States Patent [19]

Bulakiev

[11] Patent Number: 4,938,693
[45] Date of Patent: Jul. 3, 1990

[54] DENTAL IMPLANTATE

[75] Inventor: Georgi K. Bulakiev, Sofia, Bulgaria

[73] Assignee: Centar Po Subna Implantologia I Protesirane "Avangard", Sofia, Bulgaria

[21] Appl. No.: 272,559

[22] Filed: Nov. 16, 1988

[51] Int. Cl.⁵ .................................................. A61C 8/00
[52] U.S. Cl. ...................................... 433/169; 433/173
[58] Field of Search ................ 433/169, 173, 174, 175, 433/176

[56] References Cited

U.S. PATENT DOCUMENTS

| | | | |
|---|---|---|---|
| 2,880,508 | 4/1959 | Lester et al. | 433/169 |
| 3,863,344 | 2/1975 | Pillet | 433/169 |
| 4,609,354 | 9/1986 | Koch | 433/173 |
| 4,731,085 | 3/1988 | Koch | 433/173 |
| 4,793,808 | 12/1988 | Kirsch | 433/173 |
| 4,824,372 | 4/1989 | Jorneus et al. | 433/174 |

FOREIGN PATENT DOCUMENTS 655437 4/1986 Switzerland .................. 433/173

Primary Examiner—John J. Wilson
Attorney, Agent, or Firm—Herbert Dubno

[57] ABSTRACT

The dental implantate comprises a dental insert with a blank hole made therein having an inner thread. An adjuster bolt is mounted in this blank hole which is encompassed by a remote disk resting against the front of the dental insert. On the remote disk is fixed a superstructure that is fastened to the adjuster bolt. The latter has a conical sector which is encircled by a sealing ring. Outside the dental insert protrudes an adjusting bushing and on it is screwed a remote disk on which rests the superstructure. On the bottom of the blank hole in the dental insert is fixed an elastic bushing in which is screwed the adjuster bolt. The dental implantate is useful in orthopedic stomatology and its advantages are expressed in its simplified design and simple operational technics.

1 Claim, 1 Drawing Sheet

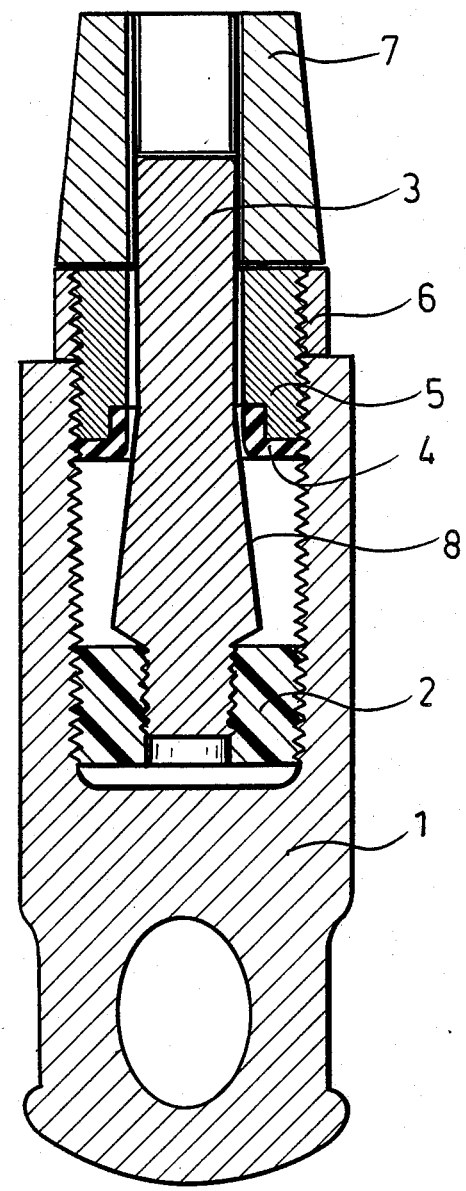

DENTAL IMPLANTATE

BACKGROUND OF THE INVENTION

The invention refers to a dental implantate that transmits and regulates chewing pressure. It will be largely used in orthopedic stomatology.

A dental implantate (1) is known comprising a dental insert with a blank hole made therein. In the inner thread of the blank hole in the dental insert is screwed an adjuster bolt. This bolt is encompassed by a remote disk that rests against the front of the dental insert. To the upper end of the adjuster bolt is fixed a superstructure.

A disadvantage of the known dental implantate is that the chewing pressure is not taken up in depth and it can not be regulated.

The object of the invention is to provide for a dental implantate with a simplified design and operation that ensures a dosed transmission of the chewing pressure which pressure is controlled in the horizontal and vertical direction of the implantate seat depth.

SUMMARY OF THE INVENTION

This object is achieved by a dental implantate comprising a dental insert with a blank hole made therein having an inner thread. In this blank hole is mounted an adjuster bolt. The latter is encompassed by a remote disk that is resting against the front of the dental insert. On the remote disk is fixed a superstructure that is fastened to the adjuster bolt. According to the invention the adjuster bolt has a conical section which is encircled by a sealing ring. This ring is fixed to a regulating bushing that is screwed in the upper part of the blank hole in the dental insert. The regulating bushing protrudes outside the dental insert and on it is screwed a remote disk on which rests the superstructure. On the bottom of the blank hole in the dental insert is fastened an elastic bushing in which is screwed the adjuster bolt.

The advantages of the invention are found in its simplified design and operation. A further advantage is the possibility for a more precise regulation of the chewing pressure in the vertical direction and possibly also in the horizontal direction.

An additional advantage is that the chewing pressure is taken up entirely in the depth of the dental insert.

BRIEF DESCRIPTION OF THE DRAWINGS

An exemplary embodiment of the invention is presented through the sole FIGURE which is a longitudinal cut of the dental implantate in its working position.

DETAILED DESCRIPTION

According to the invention the dental implantate comprises a dental insert 1 with a blank hole provided therein with a screw thread. On the bottom of the blank hole is mounted an elastic bushing 2 in the opening of which is elaborated a thread. In the elastic bushing 2 is screwed an adjuster bolt 3 having a body shaped in the form of a conical sector 8. In this sector 8 rests a sealing ring 4 which is fastened to an adjuster bushing 5 that is screwed in the upper part of the blank hole. The adjuster bushing 5 protrudes over the front of the dental insert 1 and to it is screwed a remote disk 6. Within disk 6 is fixed a superstructure 7 that is screwed on the adjuster bolt 3.

The dental implantate is mounted in the following manner: Under local anesthesia a mucoperiastalic lambo is prepared having dimensions permitting a free operation in the bone. In case of remnants from an old dental root, these are removed and the place is cleaned. Under continuous cooling with a sterile physiological solution, a bore is drilled with a consequent widening of the site for fixing of the dental insert 1. Then immediately after the necessary preparation of the opening for fixing of the implantate, the latter is mounted according to an established procedure so that the blank hole of dental insert 1 is tamped by screwing to the end of a suitable auxiliary bolt. The mucoperiastalic lambo is sewn. The dental insert remains in this position 3 to 4 months in case of the lower jaw and 4 to 6 months in case of upper jaw. When the operating dentist is convinced that the dental insert 1 is holding fast, he starts with the mounting of the dental implantate. First is made a circular opening over the auxiliary bolt which is tamping the dental insert 1 and afterwards the latter is removed by unscrewing and special compressing and retaining of dental insert 1.

The elastic bushing 2 is screwed to the end in the blank hole of dental insert 1 while the adjuster bushing 5 is screwed to the end on the sealing ring 4 around the conical sector 8.

Adjuster bushing 5 is tightened by fastening the remote disk 6. Prior thereto, several control measurements are taken of the chewing pressure value for the concrete implantate taking into consideration the mobility of the adjacent tooth -antagonist or any other from a bridge construction. The mounting of the remote disk 6 is performed in conformity to the mucose thickness so that the disk is always protruding over the level of the mucose. Thereafter the procedure is continued with traditional methods known in orthopedic stomatology, in this case—mounting of the superstructure 7 on the upper end of adjuster bolt 3 and then mounting of the crown.

I claim:
1. A dental implantate comprising:
   a dental insert whose inner walls define a blank hole with an open and a closed end;
   an adjuster bolt fastened within said hole, a section of said bolt being conical in shape;
   an elastic bushing fastened to the closed end of the blank hole of the dental insert and surrounding a portion of said adjuster bolt;
   a sealing ring surrounds a portion of said conical section;
   an adjusting bushing fixed to said sealing ring, fitted into said blank hole, and protruding outside said hole;
   a superstructure fixed to said adjuster bolt; and
   a remote disk encompassing said adjusting bushing, resting against the open end of the dental insert and contacting said superstructure.

* * * * *